(12) United States Patent
Chase

(10) Patent No.: US 6,204,672 B1
(45) Date of Patent: Mar. 20, 2001

(54) SYSTEM FOR PRODUCING PAPER PRODUCT INCLUDING A COMPACT HIGH-RESOLUTION UNDER WIRE WATER WEIGHT SENSOR ARRAY

(75) Inventor: Lee Chase, Los Gatos, CA (US)

(73) Assignee: Honeywell International Inc, Morristown, NJ (US)

( * ) Notice: Subject to any disclaimer, the term of this patent is extended or adjusted under 35 U.S.C. 154(b) by 0 days.

(21) Appl. No.: 09/558,486

(22) Filed: Apr. 25, 2000

Related U.S. Application Data

(60) Division of application No. 08/977,773, filed on Nov. 21, 1997, now Pat. No. 6,087,837, which is a continuation-in-part of application No. 08/766,864, filed on Dec. 13, 1996, now Pat. No. 5,891,306.

(51) Int. Cl.[7] .......................... G01N 27/02; G01N 27/12; G01N 33/34
(52) U.S. Cl. .......................... 324/695; 324/693; 324/694; 324/696; 162/198; 162/263; 73/53.03
(58) Field of Search .................................... 324/663, 664, 324/671, 689, 690, 693, 694, 695, 696, 699, 701, 724; 162/198, 263; 73/53.03

(56) References Cited

U.S. PATENT DOCUMENTS

| | | |
|---|---|---|
| 3,260,642 | 7/1966 | Canter . |
| 3,593,128 | 7/1971 | Perry . |
| 3,630,836 | 12/1971 | Bietry et al. . |
| 3,636,327 | 1/1972 | Troutman . |
| 3,646,434 | 2/1972 | Norwich . |
| 3,654,075 | 4/1972 | Keyes et al. . |
| 3,713,966 | 1/1973 | Lippke . |
| 3,723,712 | 3/1973 | Komline, Sr. et al. . |
| 3,723,865 | 3/1973 | Batey et al. . |
| 3,795,984 | 3/1974 | Meyer . |
| 3,811,087 | 5/1974 | Schmelzer . |
| 3,864,626 | 2/1975 | MacLean et al. . |
| 3,909,380 | 9/1975 | Day et al. . |
| 3,986,110 | 10/1976 | Overall et al. . |
| 4,135,151 | 1/1979 | Rogers et al. . |
| 4,259,632 | 3/1981 | Ahtiainen . |
| 4,314,878 | 2/1982 | Lee . |
| 4,329,201 | 5/1982 | Bolton . |
| 4,369,080 | 1/1983 | Johnson . |
| 4,398,996 | 8/1983 | Bolton et al. . |
| 4,468,611 | 8/1984 | Tward . |
| 4,474,643 | 10/1984 | Lindblad . |
| 4,514,812 | 4/1985 | Miller et al. . |
| 4,535,285 | 8/1985 | Evans et al. . |
| 4,580,233 | 4/1986 | Parker et al. . |

(List continued on next page.)

FOREIGN PATENT DOCUMENTS 0276106  7/1988 (EP) .

OTHER PUBLICATIONS

Smook, G.A., Handbook for Pulp & Paper Technologist, 2d. ed., (Angus Wilde Publications), 1992, pp. 228–229, (month unavailable).

* cited by examiner

Primary Examiner—Glenn W. Brown
(74) Attorney, Agent, or Firm—Burns Doane Swecker & Mathis

(57) ABSTRACT

A measurement apparatus for sensing three properties of materials including a fixed impedance element coupled in series with the sensor array between an input signal and a reference potential (e.g. ground). The sensor array exhibits a variable impedance resulting from changes in physical characteristics of the material. The variable impedance of the sensor array relates to changes in property of the material being sensed which can then be related to changes in other physical characteristics of the material such as weight, chemical composition, and temperature. The reduced size and increased resolution of the sensor array is particularly adaptive to a twin mesh sheetmaking system.

10 Claims, 7 Drawing Sheets

U.S. PATENT DOCUMENTS

| | | |
|---|---|---|
| 4,588,943 | 5/1986 | Hirth . |
| 4,613,406 | 9/1986 | Gess . |
| 4,648,715 | 3/1987 | Ford, Jr. et al. . |
| 4,680,089 | 7/1987 | Aral et al. . |
| 4,692,616 | 9/1987 | Hegland et al. . |
| 4,707,779 | 11/1987 | Hu . |
| 4,748,400 | 5/1988 | Typpo . |
| 4,786,529 | 11/1988 | Boissevain . |
| 4,791,353 | 12/1988 | Typpo . |
| 4,817,021 | 3/1989 | Sowerby et al. . |
| 4,827,121 | 5/1989 | Vidrine, Jr. et al. . |
| 4,840,706 | 6/1989 | Campbell . |
| 4,845,421 | 7/1989 | Howarth et al. . |
| 4,903,528 | 2/1990 | Balakrishnan et al. . |
| 4,909,070 | 3/1990 | Smith . |
| 4,921,574 | 5/1990 | Hu . |
| 4,924,172 | 5/1990 | Holmgren . |
| 4,947,684 | 8/1990 | Balakrishnan . |
| 4,957,770 | 9/1990 | Howarth . |
| 4,980,846 | 12/1990 | Chapman . |
| 4,986,410 | 1/1991 | Shields . |
| 4,990,261 | 2/1991 | Ho . |
| 4,994,145 | 2/1991 | Seymour . |
| 5,013,403 | 5/1991 | Chase . |
| 5,020,469 | 6/1991 | Boissevain et al. . |
| 5,021,740 | 6/1991 | Sarr et al. . |
| 5,022,966 | 6/1991 | Hu . |
| 5,045,798 | 9/1991 | Hendrick . |
| 5,052,223 | 10/1991 | Regnault et al. . |
| 5,067,345 | 11/1991 | Mougne . |
| 5,093,795 | 3/1992 | Lewis . |
| 5,122,754 | 6/1992 | Gotaas . |
| 5,124,552 | 6/1992 | Anderson . |
| 5,132,631 | 7/1992 | Klopfenstein et al. . |
| 5,134,380 | 7/1992 | Jonas . |
| 5,170,128 | 12/1992 | Masurat et al. . |
| 5,170,670 | 12/1992 | Fasching et al. . |
| 5,177,445 | 1/1993 | Cross . |
| 5,198,777 | 3/1993 | Masuda et al. . |
| 5,206,599 | 4/1993 | Mayer . |
| 5,208,544 | 5/1993 | McBrearty et al. . |
| 5,225,785 | 7/1993 | Mayer et al. . |
| 5,241,280 | 8/1993 | Aidun et al. . |
| 5,244,550 | 9/1993 | Inoue . |
| 5,247,261 | 9/1993 | Gershenfeld . |
| 5,262,955 | 11/1993 | Lewis . |
| 5,270,664 | 12/1993 | McMurtry et al. . |
| 5,280,250 | 1/1994 | Jayaweera et al. . |
| 5,340,442 | 8/1994 | Gess et al. . |
| 5,400,247 | 3/1995 | He . |
| 5,450,015 | 9/1995 | Mastico et al. . |
| 5,492,601 | 2/1996 | Ostermayer et al. . |
| 5,493,910 | 2/1996 | Hall et al. . |
| 5,539,634 | 7/1996 | He . |
| 5,561,599 | 10/1996 | Lu . |
| 5,563,809 | 10/1996 | Williams et al. . |
| 5,636,126 | 6/1997 | Heaven et al. . |
| 5,658,432 | 8/1997 | Heaven et al. . |
| 5,853,543 * | 12/1998 | Hu et al. ............................... 162/198 |
| 5,928,475 * | 7/1999 | Chase et al. ......................... 162/198 |
| 6,059,931 * | 5/2000 | Hu et al. ............................... 162/198 |
| 6,086,716 * | 7/2000 | Watson et al. ....................... 162/198 |
| 6,099,690 * | 8/2000 | Hu et al. ............................... 162/198 |

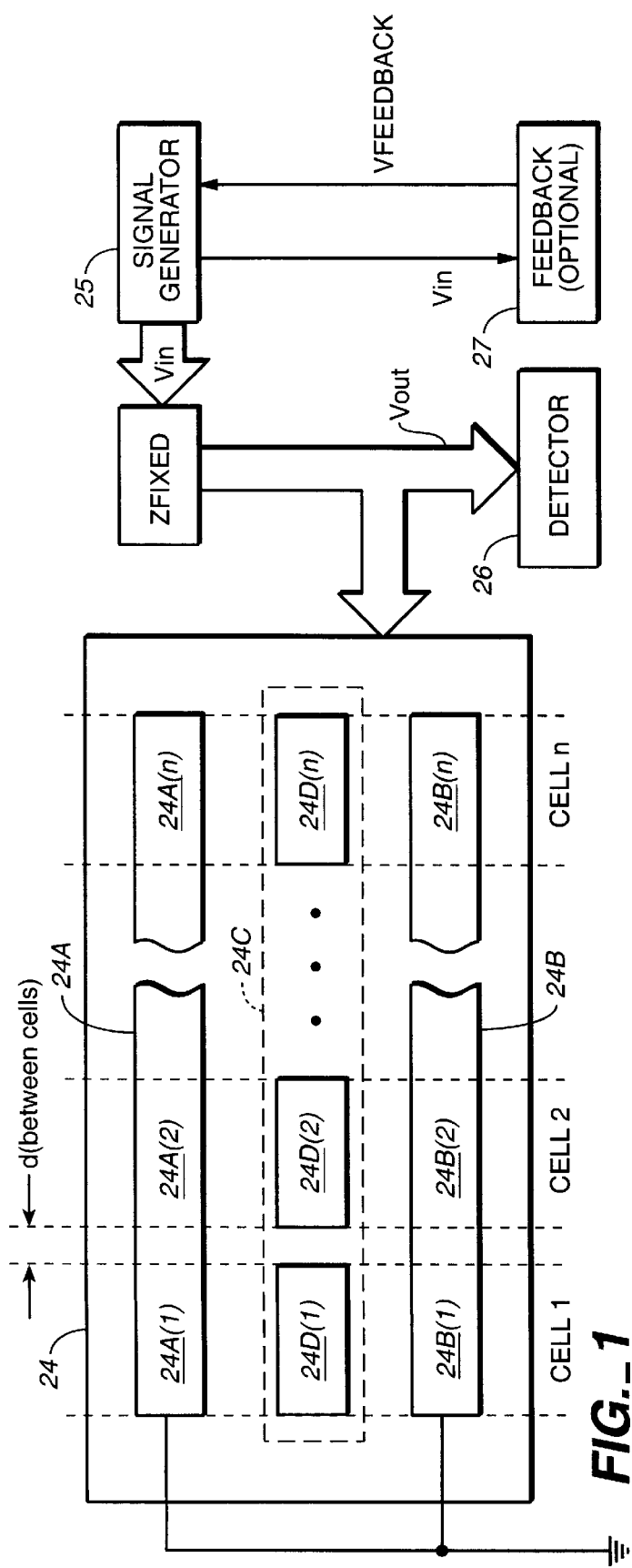
FIG._1
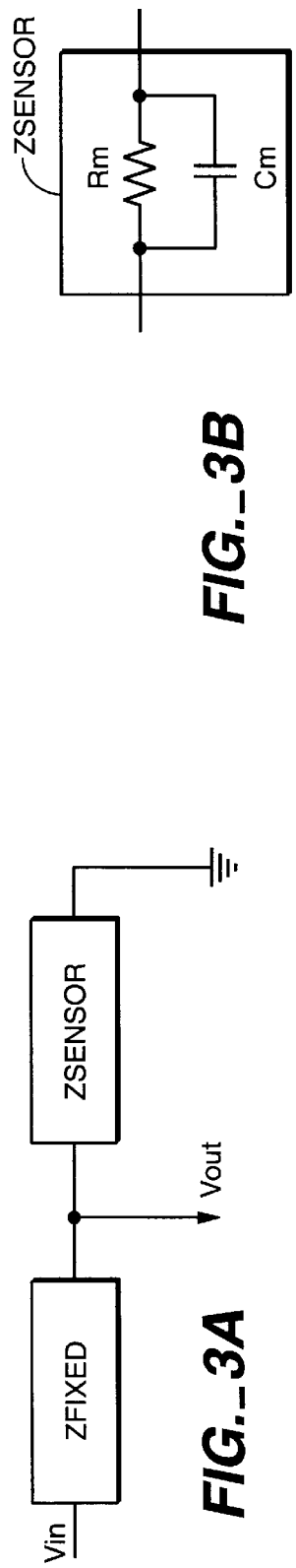
FIG._3B
FIG._3A

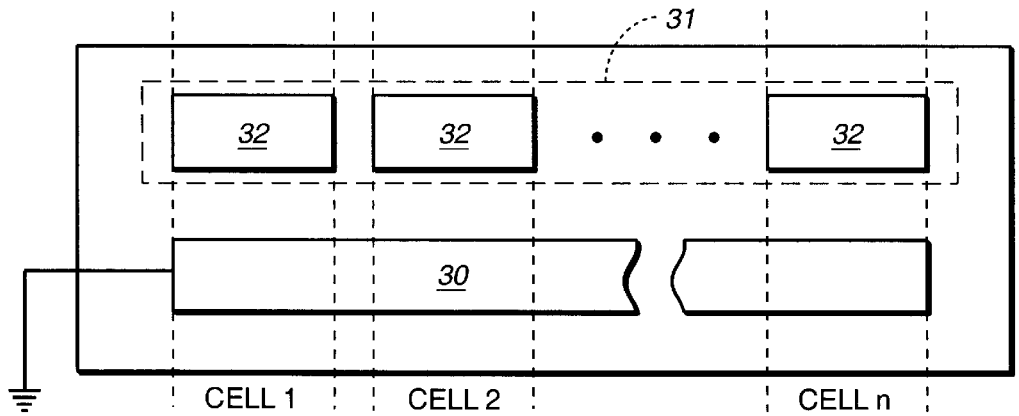
FIG._2
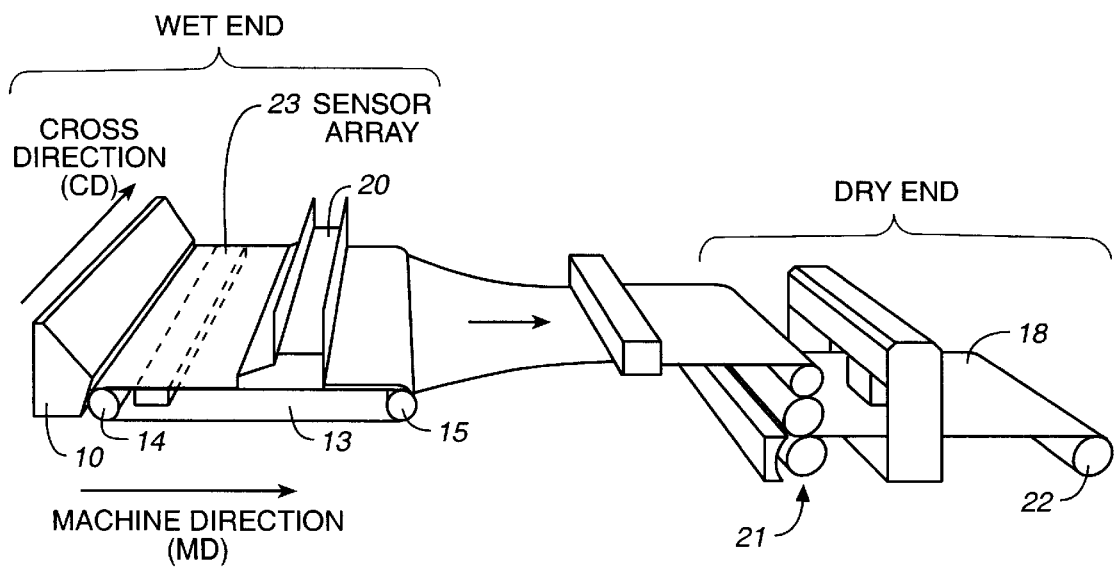
FIG._4

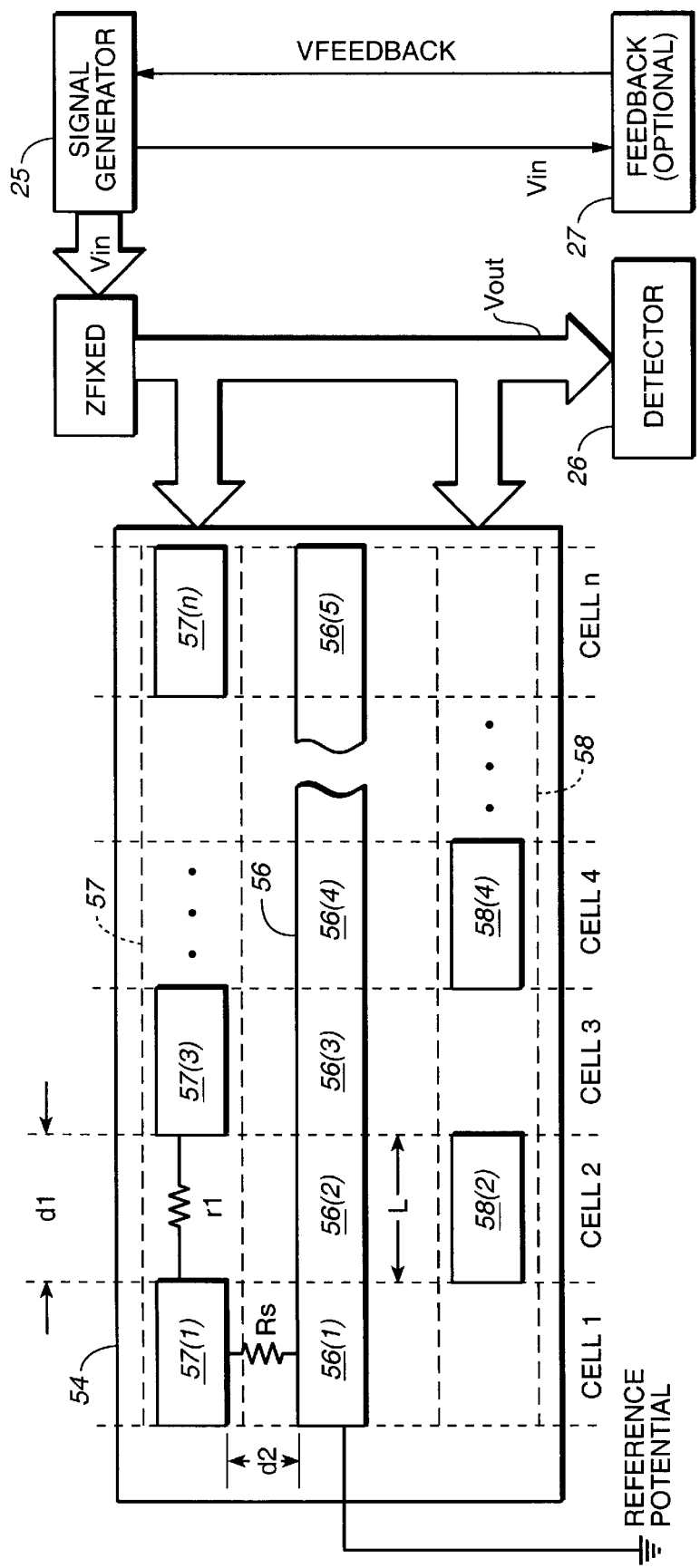
FIG._5A

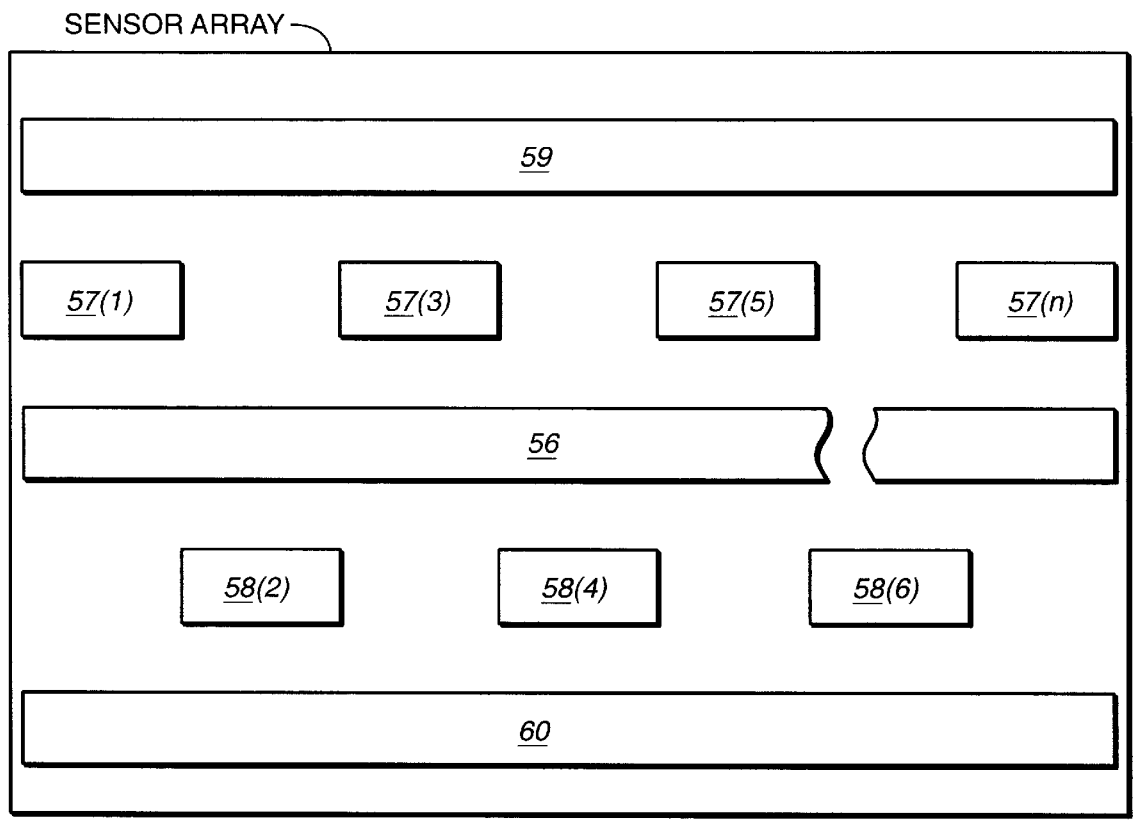
FIG._5B
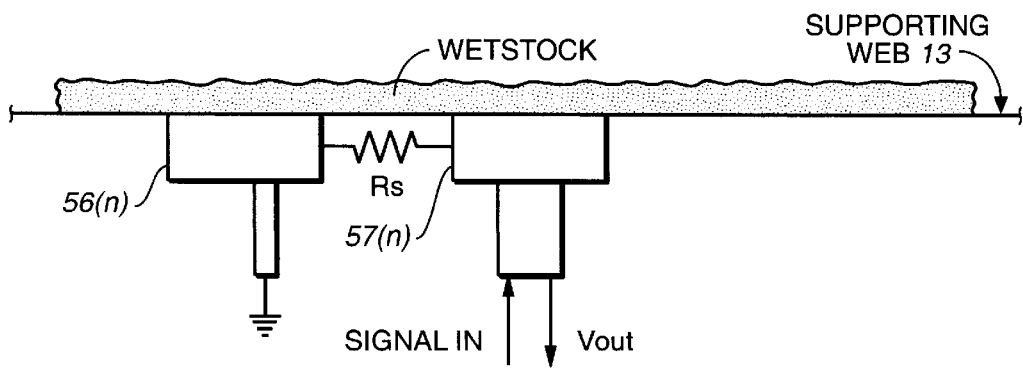
FIG._6B

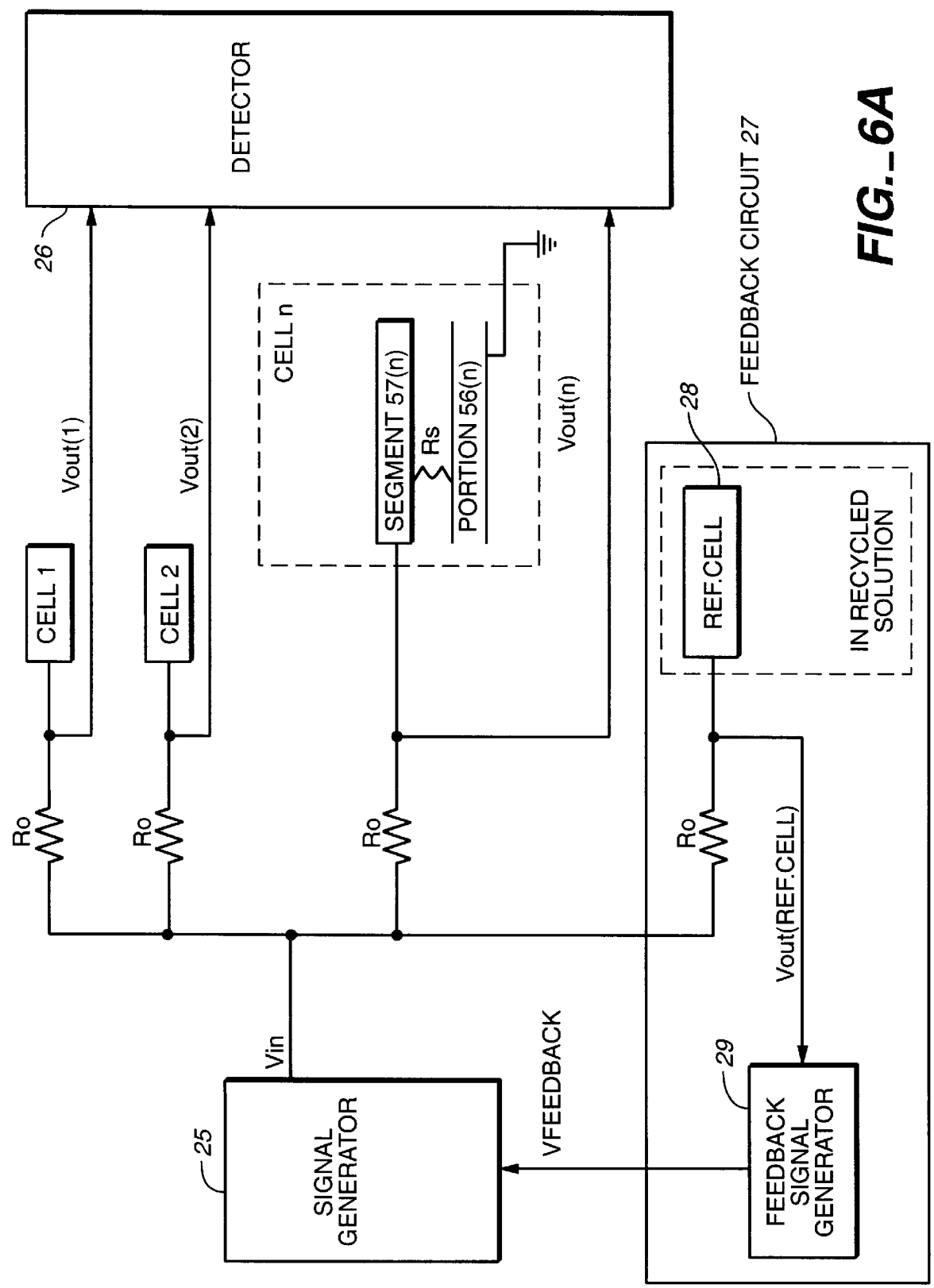
FIG._6A

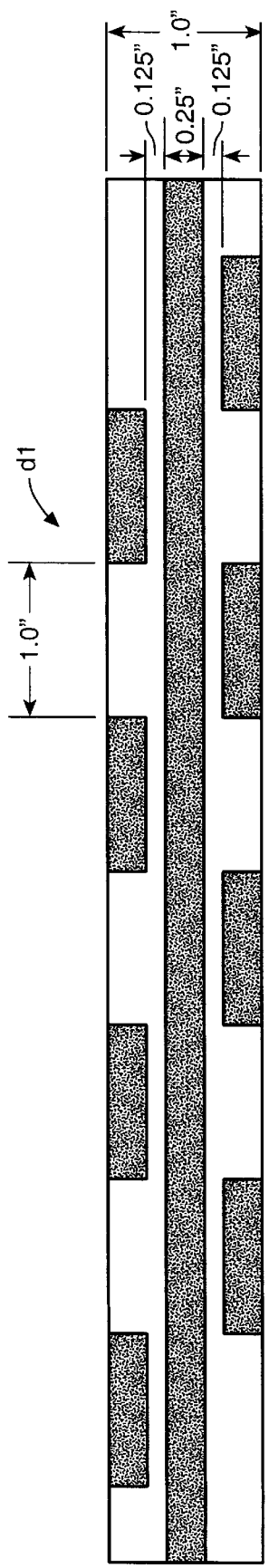
FIG._7
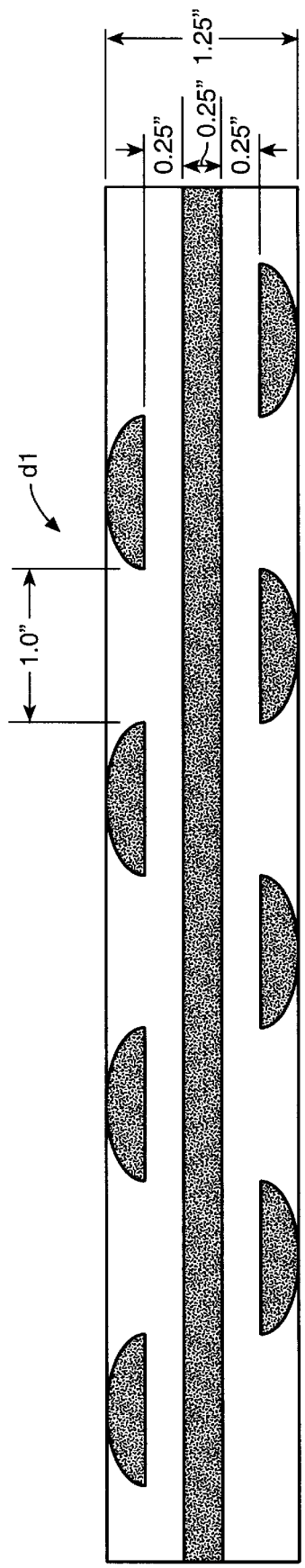
FIG._8

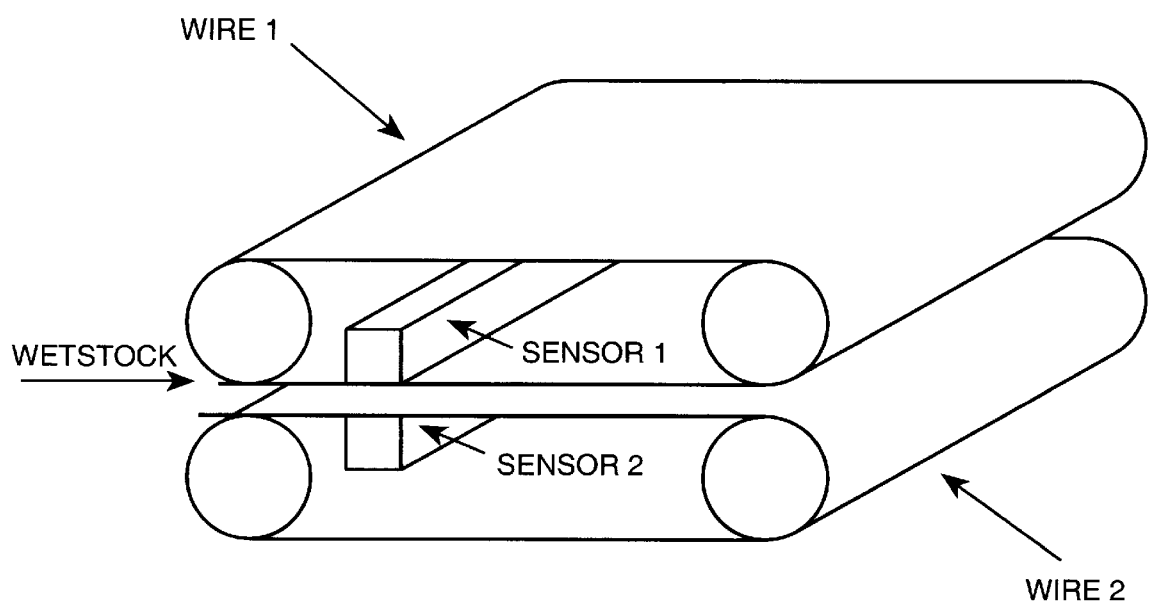
FIG._9

SYSTEM FOR PRODUCING PAPER PRODUCT INCLUDING A COMPACT HIGH-RESOLUTION UNDER WIRE WATER WEIGHT SENSOR ARRAY

CROSS REFERENCE TO RELATED APPLICATIONS

This application is a divisional of application Ser. No. 08/977,773 filed Nov. 21, 1997, now U.S. Pat. No. 6,087,837, which is a Continuation-in-Part of application Ser. No. 08/766,864 filed Dec. 13, 1996, now U.S. Pat. No. 5,891,306.

BACKGROUND OF THE INVENTION

1. Field of the Invention

The present invention generally relates to systems for controlling continuous sheetmaking systems and, more specifically, to sensors for measuring the fiber weight of wetstock in a papermaking machine.

2. State of the Art

In the alt of modem high-speed papermaking, it is well known to continuously measure certain properties of the paper material in order to monitor the quality of the finished product. These on-line measurements often include basis weight, moisture content, and sheet caliper (i.e., thickness). The measurements can be used for controlling process variables with the goal of maintaining output quality and minimizing the quantity of product that must be rejected due to upsets in the manufacturing process.

The on-line sheet property measurements are often accomplished by scanning sensors that periodically traverse the sheet material from edge to edge. For example, a high-speed scanning sensor may complete a scan in a period as short as twenty seconds, with measurements being read from the sensor at about 50 milliseconds intervals. It is also know that a series of stationary sensors can be used to make similar on-line measurements.

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a de-watering, i.e., water removal, system. A typical forming section of a papermaking machine includes an endless traveling papermaking mesh fabric or wire which travels over a series of water removal elements such as table rolls, foils, vacuum foils, and suction boxes. As the material travels on the mesh fabric over the series of water removal elements, there is a distinct line of demarcation showing a change in the state of the stock from an extremely wet state to a relatively dryer state. This visible line of demarcation (referred to as the dry line) is characterized in that one side of the dry line has a glossy appearance (i.e. wet state) and the other side of the line has a non-glossy appearance (i.e., relatively dry state). The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Other papermaking devices well known in the art are described for example in U.S. Pat. No. 5,400,258.

In another type of papermaking system (referred to as a twin wire machine), two meshes are used. A first mesh resides on the top of the stock and a second mesh resides underneath and supports the stock. Water is removed from the top by vacuum and from the bottom by gravity (and in some cases also by vacuum). The advantage to this type of system is that water is removed at a much quicker rate than in the previously described single mesh system, resulting in a faster machine speed, a more controllable process, and more uniform paper product. In addition, this system is smaller since it requires less mesh length, has a shorter drying time, and consequently, reduced processing costs.

Many factors influence the rate at which water is removed which ultimately affects the quality of the paper produced. As is apparent. it would be advantageous to monitor the dynamic process so as to, among other things, predict and control the dry stock weight of the paper that is produced.

It is conventional to measure the moisture content on leaving the main dryer section or at the take up reel employing scanning sensors. Such measurement may be used to adjust the machine operation toward achieving desired parameters. One technique for measuring moisture content is to utilize the absorption spectrum of water in the infra-red. Monitoring or gauge apparatus for this purpose is commonly in use. Such apparatus conventionally uses either a fixed gauge or a gauge mounted on a scanning head which is repetitively scanned transversely across the web at the exit from the dryer section and/or upon entry to the take up reel, as required by the individual machines. The gauges typically use a broad-band infra-red source and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (sometimes called "reflective" type) in which the source and detector are in a single head on one side of the web, the detector responding to the amount of source radiation scattered from the web.

SUMMARY OF THE INVENTION

The present invention is a measurement apparatus including a compact high resolution sensor array. In general, the measurement apparatus includes a fixed impedance element coupled in series with a detection cell in the sensor array which is coupled between an input signal and a reference potential (e.g. ground) and which has a variable impedance. The fixed impedance element and the detection cell form a voltage divider network such that changes in impedance of the detection cell results in changes in voltage on the output of the measurement system. The impedance of the detection cell represents the impedance of the physical configuration of electrodes within the sensor array and the material residing between and in close proximity to the electrodes. The impedance relates to the property of the material being measured.

In one embodiment, the measurement apparatus is used to measure the conductivity of an aqueous mixture (referred to as wetstock) in a papermaking system. In this case, the conductivity of the wetstock is high and dominates the measurement. The conductivity of the wetstock is directly proportional to the total water weight within the wetstock, consequently providing information which can be used to monitor and control the quality of the paper sheet produced by the papermaking system.

In another embodiment, the measurement apparatus is used to measure the weight of plastic. In this application the conductivity is negligible and the capacitive impedance is inversely proportional to the dielectric constant and the amount of plastic between the electrodes of the measurement apparatus.

In still another embodiment, the fixed impedance element is embodied as an inductor and the input signal is an analog signal. In this embodiment, the impedance of the inductor can be selected to be a particular magnitude by setting the frequency of the input signal. The advantage of this embodiment is that for optimum sensor sensitivity the impedance of the fixed impedance element can be set to the same range as the impedance of the sensor. Hence, in the case in which the impedance of the sensor varies due to fluctuations in operating conditions of the system or the material being sensed, the impedance of the inductor can be customized to match the sensor impedance without any hardware changes.

In one embodiment of the present invention, the sensor array includes first and second elongated segmented side electrodes and a center elongated electrode spaced-apart and centered between the side electrodes all in essentially the same plane. Segments in the two side electrodes are configured such that the segments in the first segmented electrode are staggered with respect to segments in the second segmented electrode. A cell within the array is defined as including one of the segments and a corresponding portion of the center electrode opposite to that segment. In a second embodiment, the sensor array can also include additional grounded electrodes situated along side each of the first and second segmented electrodes so as to guard against current leakage to conductors in the vicinity of the electrodes.

In one embodiment, the segment of each cell is independently coupled to an input signal provided by a signal generator through an impedance element. In one embodiment, the impedance elements are implemented as resistive elements. Each cell forms a voltage divider network made-up of the resistive element coupled between the signal generator and the segment of a given cell and of a resistance resulting from the effective water resistance between the segment and its corresponding opposing portion of the center electrode. The output of each cell is taken from the segment, i.e., the point between the resistive element and the cell. As the conductance of the aqueous mixture changes so does the output voltage of the cell. The output voltage of each cell is coupled to a detector which, in one embodiment, includes circuitry for enhancing the signal such as an amplifier for amplifying the output signal from each cell and a rectifier. In one embodiment of the present invention the detector includes circuitry for converting the output voltages from each cell into data relating to the weight of the aqueous mixture or to other aqueous mixture characteristics.

The apparatus of the present invention may optionally include a feedback circuit which is used to adjust the input signal provided from the signal generator to compensate for changes in properties of the aqueous mixture that is not being sensed, but that also may affect the output voltages of the cells. The feedback circuit includes a reference cell having a similar electrode configuration as a single cell within the array. The reference cell also has a segment coupled to the signal generator through a resistive element and is placed in recycled aqueous mixture from the array and consequently the reference cell is immersed in an aqueous mixture having essentially the same chemical and temperature properties as the aqueous mixture that the cell array is in. Furthermore, the characteristic that is being measured (e.g., weight changes) is held constant on the reference cell while all other characteristics which may affect the output voltage from the reference cell are allowed to fluctuate. As a result, all voltage changes from the reference cell are due to property changes of the aqueous mixture (e.g., temperature, chemical composition) other than the characteristic that is being measured (e.g., weight changes). The voltage from the reference cell is then converted into a feedback signal and then used to adjust the signal from the generator to compensate for changes in aqueous mixture conductivity other than changes in weight.

In one embodiment of the present invention, the apparatus is used in a sheetmaking system which includes a web. The sensor is positioned under the web such that it is either parallel to the cross-direction or machine direction of the sheetmaking system and is in contact with the wetstock. In another embodiment the sensor is placed under the web prior to the dry line of the sheetmaking system. In still another embodiment, sensors according to the present invention are used in a twin web (also referred to as twin wire) sheetmaking system wherein a first sensor is positioned under a first wire and a second sensor is positioned under a second wire.

BRIEF DESCRIPTION OF THE DRAWINGS

FIG. 1 shows a block diagram of a measurement apparatus having a first sensor array configuration.

FIG. 2 shows a second sensor array configuration.

FIG. 3A shows a basic electrical diagram of a measurement apparatus using a sensor block having a variable impedance and 3B shows that equivalent circuit of the sensor block shown in FIG. 3A.

FIG. 4 shows a sheetmaking system including a sensor array situated beneath the web of the system.

FIG. 5A shows a block diagram of a measurement apparatus having a first embodiment of a sensor array in accordance with the present invention.

FIG. 5B shows a second embodiment of the sensor array in accordance with the present invention having additional grounded electrodes.

FIG. 6A shows an electrical representation of an embodiment of the measurement apparatus shown in FIG. 5A.

FIG. 6B shows a cross-sectional view of a cell used within the sensor array of the present invention and its general physical position within a sheetmaking system in accordance with one implementation of the sensor array of the present invention.

FIG. 7 shows a first embodiment of the sensor array of the present invention.

FIG. 8 shows a second embodiment of the sensor array of the present invention.

FIG. 9 shows a twin wire sheetmaking machine including sensors according to the present invention associated with each of the wires.

DESCRIPTION OF THE PREFERRED EMBODIMENTS

The present invention is a measurement apparatus for measuring properties of material and, in one embodiment, for determining the weight of fiber in wetstock in a sheet making system. In the following description, numerous specific details are set forth, such as particular uses of the system, resistive values frequencies, etc. in order to provide a thorough understanding of the present invention. It will be obvious, however, to one skilled in the art that these specific details need not be employed to practice the present invention. In other instances, well understood sheetmaker system structures have not been described in detail in order to avoid unnecessarily obscuring the present invention.

FIG. 1 shows a moisture measurement system described in U.S. Pat. No. 5,891,306 assigned to the assignee of the present application which measures the conductivity of the water in the stock material using a sensor array (FIG. 1). The conductivity of the water is proportional to the water weight. The sensor array includes two elongated grounded electrodes 24A and 24B and a segmented electrode 24C. Measuring cells (cell1, cell2, . . . celln) each include a segment of electrode 24C and a corresponding portion of the grounded electrodes (24A and 24B) opposite the segment. Each cell detects the conductivity of the paper stock and specifically the water portion of the stock residing in the space between the segment and its corresponding opposing portions of grounded electrode. U.S. Pat. No. 5,896,306 discloses a variation of the above described electrode configuration having a single elongated grounded electrode 30 and a segmented electrode 32 (FIG. 2).

FIG. 3A is a block diagram showing a portion of the measuring apparatus as described in U.S. Pat. No. 5,891,306 which includes a fixed impedance element (Zfixed) coupled in series with a variable impedance block (Zsensor) between an input signal (Vin) and a reference potential (e.g. ground). The fixed impedance element may be embodied as a resistor, an inductor. a capacitor, or a combination of these elements. The fixed impedance element and the impedance of Zsensor form a voltage divider network such that changes in impedance of Zsensor results in changes in voltage on Vout. The impedance block Zsensor shown in FIG. 3A is representative of electrodes in the sensor array and the material residing between the electrodes. The impedance block. Zsensor, can also be represented by the equivalent circuit shown in FIG. 3B, where Rm is the resistance of the material between the electrodes and Cm is the capacitance of the material between the electrodes.

The sensor array is sensitive to three physical properties of the material being detected: the conductivity or resistance, the dielectric constant, and the proximity of the material to the sensor. Depending on the material, one or more of these properties will dominate. The material capacitance depends on the geometry of the electrodes, the dielectric constant of the material, and its proximity to the sensor. For a pure dielectric material, the resistance of the material is infinite (i.e. Rm=∞) between the electrodes and the sensor measures the dielectric constant of the material. Alternatively, for a highly conductive material, the resistance of the material is much less than the capacitive impedance (i.e., $Rm \ll Z_{Cm}$), and the sensor measures the conductivity of the material.

To measure material properties, Vin is coupled to the voltage divider network shown in FIG. 3A and changes in the variable impedance block (Zsensor) is measured on Vout. In this configuration the sensor impedance, Zsensor, is:

$$Zsensor = Zfixed * Vout/(Vin-Vout).\qquad\text{Eq. 1}$$

The changes in impedance of Zsensor relates to physical characteristics of the material such as material weight, temperature, and chemical composition. It should be noted that optimal sensor sensitivity is obtained when Zsensor is approximately the same as or in the range of Zfixed.

In one particular embodiment, the sensor of the present invention is for measuring physical characteristics of an aqueous mixture (referred to as wetstock) in a sheetmaker system by detecting conductivity changes of the wetstock. FIG. 4 shows a typical sheetmaking system for producing a continuous sheet of paper material 18 including a headbox 10, a steambox 20, a calendaring stack 21, a take-up reel 22 and sensor array 23. In the headbox 10, actuators are arranged to control discharge of wetstock onto supporting web 13. The sheet 18 travels between rollers 14 and 15, and passes through a calendaring stack 21. The calendaring stack 21 includes actuators 24 that control the compressive pressure applied across the paper web. The finished sheet product is collected on a reel 22. In practice, the portion of the papermaking process near the headbox is referred to as the "wet end". while the portion of the process near the takeup reel is referred to as the "dry end". The wet end is essentially the water removal stage which includes the water removal elements such as table rolls, Foils, vacuum foils, and suction boxes while the dry end is essentially the drying stage which includes steam heated dryers and hot air. The sensor array of a measuring apparatus as described above resides beneath supporting web 13 for sensing certain properties of the wetstock on the web in the wet end of the sheetmaking machine. Further, in one embodiment, the sensor is placed beneath supporting web 13 prior to the dry line.

In both of the sensor array configurations shown in FIGS. 1 and 2, the spacing between the segments are such that the resistance between adjacent segments (e.g., between 24D(1) and 24D(2)) is much greater than the resistance between a given segment and its corresponding opposing grounded electrode section within the cell (e.g., between 24A(1) and 24D(1)) so as to essentially eliminate cross-talk between adjacent segments and hence inaccuracies in the cell measurements. However, these spaces between the segments represent a "dead space" in which no measurements are taken.

In systems having compacted water removal stages requiring high water weight measurement resolution and having less space to place the sensor array, it is advantageous to make the spacing between cells as small as possible thereby increasing the resolution of the sensor while reducing its size.

FIG. 5A illustrates a block diagram of a measurement apparatus including a signal generator 25, detector 26, optional feedback circuit 27, and including a compact, high resolution embodiment of the sensor array 54 of the present invention. Sensor array 54 includes a first elongated electrode 56 coupled to a reference potential (e.g. ground) having electrode portions 56(1)–56(n) and includes elongated segmented electrodes 57 and 58 parallel to, in the same plane as, and on opposite sides, respectively, of electrode 56. Segmented electrode 57 is made-up of segments 57(1), 57(3) . . . 57(n) and segmented electrode 58 is made-up of segments 58(2), 58(4) . . . 58(n−1). The segments of electrodes 57 and 58 are configured with respect to each other such that segments in electrode 57 are staggered with respect to segments in electrode 58. A cell within array 54 is defined as including a segment from either of electrodes 57 or 58 and the portion of electrode 56 opposite that segment. For example, cell 1 includes segment 57(1) and portion 56(1). When used in the system as shown in FIG. 4, sensor array 54 resides beneath and in contact with supporting web 13 and can be positioned either parallel to the machine direction (MD) or to the cross-direction (CD) depending on the type of information that is desired. It should also be noted that to determine the weight of fiber in a wetstock mixture by measuring its conductivity using the sensor array shown in FIG. 5A, the webstock must be in a state such that all or most of the water is held by the fiber. This state occurs prior to the occurrence of the dry line as seen on the mesh fabric as the stock travels on the mesh. In this state, the water weight of the wetstock relates directly to the fiber weight and the conductivity of the water weight can be measured and used to determine the weight of the fiber in the wetstock.

Each cell is independently coupled to an input voltage (Vin) from signal generator 25 through an impedance element Zfixed and each provides an output voltage to voltage detector 26 on bus Vout. Signal generator 25 provides Vin. In one embodiment Vin is an analog waveform signal, however other signal types may be used such as a DC signal. In the embodiment in which signal generator 25 provides a waveform signal it may be implemented in a variety of ways and typically includes a crystal oscillator for generating a sinewave signal and a phase lock loop for signal stability. One advantage to using an AC signal as opposed to a DC signal is that it may be AC coupled to eliminate DC off-set.

Detector 26 includes circuitry for detecting variations in voltage from each of the segments in electrodes 57 and 58 and any conversion circuitry for converting the voltage variations into useful information relating to the physical characteristics of the aqueous mixture. Optional feedback circuit 27 includes a reference cell having similarly configured electrodes as a single cell within the sensor array. The reference cell functions to respond to unwanted physical characteristic changes in the aqueous mixture other than the physical characteristic of the aqueous mixture that is desired to be measured by the array. For instance, if the sensor is detecting voltage changes due to changes in weight, the reference cell is configured so that the weight remains constant. Consequently, any voltage/conductivity changes exhibited by the reference cell are due to aqueous mixture physical characteristics other than weight changes (such as temperature and chemical composition). The feedback circuit uses the voltage changes generated by the reference cell to generate a feedback signal (Vfeedback) to compensate and adjust Vin for these unwanted aqueous mixture property changes (to be described in further detail below). It should also be noted that the non-weight related aqueous mixture conductivity information provided by the reference cell may also provide useful data in the sheetmaking process. FIG. 5B shows an embodiment of the sensor array shown in FIG. 5A having additional grounded elongated elements 59 and 60 each adjacent to electrode segments 57 and 58, respectively.

FIG. 6A illustrates an electrical representation of a measuring apparatus including cells 1–n of sensor array 54. As shown, each cell is coupled to Vin from signal generator 25 through an impedance element which, in this embodiment, is resistive element Ro. Referring to cell n, resistor Ro is coupled to segment 57(n) and the portion 56(n) (opposite segment 57(n)) is coupled to ground. Also shown in FIG. 6A is resistor Rs which represents the conductance of the aqueous mixture between the segments and the grounded portion. Resistors Ro and Rs form a voltage divider network between Vin and ground.

The measuring apparatus shown in FIG. 6A is based on the concept that the conductivity Rs of the aqueous mixture and the weight /amount of an aqueous mixture are inversely proportional. Consequently, as the weight increases/ decreases, Rs decreases/increases. Changes in Rs cause corresponding fluctuations in the voltage Vout as dictated by the voltage divider network. The voltage Vout from each cell is coupled to detector 26. Hence, variations in voltage directly proportional to variations in conductivity of the aqueous mixture are detected by detector 26 thereby providing information relating to the weight and amount of aqueous mixture in the general proximity above each cell.

Detector 26 may include means for amplifying the output signals from each cell and in the case of an analog signal will include a means for rectifying the signal to convert the analog signal into a DC signal. In one implementation well adapted for electrically noisy environments, the rectifier is a switched rectifier including a phase lock-loop controlled by Vin. As a result, the rectifier rejects any signal components other than those having the same frequency as the input signal and thus provides an extremely well filtered DC signal. Detector 26 also typically includes other circuitry for converting the output signals from the cell into information representing particular characteristics of the aqueous mixture.

FIG. 6A also shows feedback circuit 27 including reference cell 28 and feedback signal generator 29. The concept of the feedback circuit 27 is to isolate a reference cell such that it is affected by aqueous mixture physical characteristic changes other than the physical characteristic that is desired to be sensed by the system. For instance, if weight is desired to be sensed then the weight is kept constant so that any voltage changes generated by the reference cell are due to physical characteristics other than weight changes. In one embodiment, reference cell 28 is immersed in an aqueous mixture of recycled water which has the same chemical and temperature characteristics of the water in which sensor array 54 is immersed in. Hence, any chemical or temperature changes affecting conductivity experienced by array 54 is also sensed by reference cell 28. Furthermore, reference cell 28 is configured such that the weight of the water is held constant. As a result voltage changes Vout(ref. cell) generated by the reference cell 28 are due to changes in the conductivity of the aqueous mixture, caused from characteristic changes other than weight. Feedback signal generator 29 converts the undesirable voltage changes produced from the reference cell into a feedback signal that either increases or decreases Vin and thereby cancels out the affect of erroneous voltage changes on the sensing system. For instance, if the conductivity of the aqueous mixture in the array increases due to a temperature increase, then Vout(ref. cell) will decrease causing a corresponding increase in the feedback signal. Increasing Vfeedback increases Vin which, in turn, compensates for the initial increase in conductivity of the aqueous mixture due to the temperature change. As a result, Vout from the cells only change when the weight of the aqueous mixture changes.

It should be noted that the sensor array 54 shown in FIG. 5A may also be implemented with two additional grounded electrodes 59 and 60 (FIG. SB) on each side of electrodes 57 and 58 to eliminate the possibility of current leakage to nearby grounded conductors.

FIG. 6B also illustrates the cross-section of single cell electrode configuration from sensor array 54 with respect to a sheetmaking system in which segment 57(n) and portion 56(n) reside directly under the web 13 immersed within the aqueous mixture.

It should be noted that sensor array 24 (FIG. 1) requires a space d(cell separation) between adjacent segments (e.g. 24D(1), 24D(2), . . . 24D(n)) to minimize cross-talk between adjacent segments and consequently between detection cells. Consequently, no conductivity measurement is made in this space. (sometimes referred to as "dead" zone"). In contrast, sensor array 54 does not have dead zones between cells since two sets of segments (i.e., elongated electrodes 57 and 58) are staggered on opposite sides of the center electrode 56 such that detection cells have little or no space between them resulting in essentially no "dead space". Consequently, sensor array 54 has increased measurement resolution when compared to sensor array 24.

In addition, the size of sensor array 54 can be significantly reduced to adapt it for use in a twin wire sheetmaking system. The twin wire sheetmaking system is smaller than a conventional single wire system and as a result, size becomes an important consideration in the design of the sensor array. One manner in which to minimize the size of sensor array 54 is to reduce the spacing d2 (FIG. 5A) between each of the segmented electrodes (57 and 58) and the corresponding center electrode (56) and/or reduce the length L of the segments. However, these design variations are interdependent. Specifically, the distance d1 between adjacent segments (e.g., between 57(1) and 57(3), FIG. 5A) is directly proportional to the effective resistance (r1) between the electrodes. Similarly, the distance d2 between an electrode segment and its corresponding opposite electrode portion (e.g. between 57(1) and 56(1)) is directly proportional to the effective resistance Rs between the segment and electrode portion. To minimize cross-talk between adjacent segments, r1 must be much greater than Rs. This essentially means that the distance d1 must be sufficiently greater than the distance d2 to ensure that no interaction between adjacent segments occurs. Hence, how close electrodes 57 and 58 are placed to the center electrode 56 is dependent on the spacing between adjacent segments.

Furthermore, the distance d2 is determined by the depth of water that is being measured (referred to as the depth of penetration of the electric field between a given segment and its opposing electrode portion). Specifically, a cell having a spacing d2 between electrodes can measure the characteristic of a depth of water of d2 or less. Any water greater than that depth is essentially non-existent to the electrode. For instance if an electrode sensor having a spacing d2 is placed in a depth of water d2+n. it will detect characteristic changes up to d2 above it. However, the additional water +n above the d2 depth has no affect on the electrode. Hence, depth of liquid or substance being measured must also be taken into consideration when reducing d2.

In addition, the resistance Rs is also inversely related to segment length L. Hence, although reducing the length L is desirable so as to reduce the size of the sensor array, reducing L increases Rs which may require increasing r1 and d1 (and the size of the array) since r1 must be much greater than Rs to eliminate cross-talk. Consequently, it is necessary to take into consideration, all of the design parameters when adjusting the length L and spacings d1 and d2 to ensure that all design criteria are met.

In one embodiment of the sensor array shown in FIG. 7 the total sensor array width is one inch. The spacing d2 between a segment and its corresponding opposite electrode portion is 0.125 inch, which would be appropriate for thin water layer as found on fine paper machines. The width of the electrodes 56, 57, and 58 are 0.25 inch, thus providing an extremely compact sensor array adapted for use in a twin wire sheetmaking system. FIG. 9 shows a twin wire sheetmaking system having a sensor placed in close proximity to each of the wires to detect conductivity changes as described above.

FIG. 8 shows a second embodiment of the sensor array having a width of 1.25 inches and which has a wider d2 spacing of 0.25 inch as would be used for measuring thicker water layers found in heavier weight paper products such as on paper bag kraft machines (e.g., paper grocery bags). Specifically, the more fiber used in the feedstock for a heavier paper weight, the more water is used. Consequently, in this machine a wider space d2 is required to measure the thicker water layers. However, widening space d2 also increases Rs. To ensure that no cross-talk occurs r1 needs to be much greater than Rs. Hence, in order to facilitate this design criteria the embodiment shown in FIG. 8 modifies the shape of the segments to effectively increase the average space d1 between adjacent segments, hence increasing r1 to safeguard against cross-talk. In should be understood that the shape of the elements are not restricted to the half moon shape. Specifically, any shape that effectively increases the average space d1 could also be substituted for the shapes shown in FIG. 8.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A system for producing a paper product from a feedstock material comprising:

a headbox for dispensing said stock material;

a water removal stage for receiving said dispensed stock material having at least one webbed conveyor belt, said at least one webbed conveyor belt having a first region on which said stock material is dispensed and a second region wherein said water is removed, wherein water is removed from said dispensed material through said at least one webbed conveyor belt to produce a web of material;

a measurement apparatus including a fixed impedance portion and at least one sensor array coupled to said fixed impedance portion between a signal source and a reference potential, said at least one sensor array having a variable impedance such that changes in properties of said stock material causes changes in impedance of said at least one sensor array, said at least one sensor array being placed in close proximity to said at least one webbed conveyor belt, said at least one sensor array including:

a first elongated electrode coupled to said reference potential and second and third elongated segmented electrodes parallel to and essentially in the same plane as said first elongated electrode, wherein segments within said second and third electrodes are configured with respect to each other such that segments in said second electrode are staggered with respect to segments in said third electrode; and a drying stage for drying said web of material to form said paper product.

2. The system as described in claim 1 wherein said second and third electrodes are coupled to said fixed impedance.

3. The system as described in claim 2 wherein said fixed impedance portion comprises a plurality of resistive elements and each of said segments within said second and third electrodes are each coupled to one of said plurality of resistive elements.

4. The system as described in claim 3 further including fourth and fifth electrodes coupled to said reference potential being spaced-apart and residing adjacent to said second and third electrodes.

5. The system as described in claim 1 wherein said properties include dielectric constant, conductivity, and proximity of said material.

6. The system as described in claim 5 wherein said apparatus further comprises a means for correlating said changes in said properties to fluctuations in physical characteristics of said material including material weight, chemical composition, and temperature.

7. The system as described in claim 1 wherein said fixed impedance portion element is one of an inductive element, capacitive element, and combinations of resistive, capacitive, and inductive elements each having an associated impedance and said signal source had an associated frequency and wherein said associated impedance of said one of said inductive element, said capacitive element, and said combinations of elements is set to a particular magnitude by adjusting said signal source's associated frequency to a given magnitude.

8. The system as described in claim 7 wherein said at least one sensor array has an associated impedance and said signal source's associated frequency is adjusted such that said at least one sensor array fixed impedance and said impedance of said one of said inductive element, said capacitive element, and said combinations of elements are approximately equal.

9. The system as described in claim 1 comprising first and second webbed conveyor belts and first and second sensor arrays, wherein said first sensor array is placed in close proximity to said first webbed belt and said second sensor array is placed in close proximity to said second webbed belt.

10. The system as described in claim 1 wherein said segments have a shape other than one of a rectangular and square shape and wherein said shape facilitates obtaining a greater average space between adjacent segments in each of said second and third electrodes.

* * * * *